United States Patent [19]
Vijg et al.

[11] Patent Number: 5,814,491
[45] Date of Patent: Sep. 29, 1998

[54] METHOD OF AND APPARATUS FOR DIAGNOSTIC DNA TESTING

[76] Inventors: Jan Vijg, 16 High Rock Ter., Newton, Mass. 02167; Daizong Li, 25 Queensberry St., Apt. 15, Boston, Mass. 02215

[21] Appl. No.: 789,503

[22] Filed: Jan. 27, 1997

Related U.S. Application Data

[63] Continuation of Ser. No. 471,249, Jun. 6, 1995, abandoned.

[51] Int. Cl.⁶ .................................................. C12P 19/34
[52] U.S. Cl. ........................................ 435/91.2; 435/91.1
[58] Field of Search ................................ 435/91.2, 91.1, 435/6

[56] References Cited

U.S. PATENT DOCUMENTS

| | | | |
|---|---|---|---|
| 4,683,202 | 7/1987 | Mullis ........................................ | 435/91 |
| 5,068,176 | 11/1991 | Vijg et al. .................................. | 435/6 |
| 5,340,728 | 8/1994 | Grosz et al. ........................... | 435/91.2 |
| 5,364,759 | 11/1994 | Caskey et al. ............................. | 435/6 |

FOREIGN PATENT DOCUMENTS

| | | | |
|---|---|---|---|
| 0349024A1 | 4/1989 | European Pat. Off. .......... | C12Q 1/68 |
| WO92/13101 | 1/1992 | WIPO .............................. | C12Q 1/68 |
| WO94/11730 | 9/1993 | WIPO ......................... | G01N 27/447 |

OTHER PUBLICATIONS

Berg et al. (1995) Clin. Chem. 41:1461–66.
Repp et al. (1995) Leukemia 9:210–15.
Repp et al. (1993) J. Clin. Microbiol. 31:1095–1102.
Avner et al. (1994) Hum. Reprod. 9:1676–80.
Dreesen et al. (1995) Molecular Hum. Reprod. 10:743–748.
Tenorio et al. (1993) J. Virol. Methods 44:261–69.
Reubel et al. (1995) Arch. Virol. 140:1049–60.
Levinson et al. (1992) Reliable gender screening for human preimplantation embryos using multiple DNA target sequences. Human Reproduction 7:1304–13.
Zazzi et al. (1993) Simultaneous Amplification of Multiple HIV–1 DNA sequences from clinical specimens by using nested–primer polymerase chain reaction. *AIDS Res. Human Retroviruses* 9:315–320.
Uitterlinden and Vijg (1990) Appl. Theoret. Electrophor., 1:175–9.
Vijg et al. (1994) Mutation Res., 308:205–214.
Meerman et al. (1993) Am. J. Hum. Genet., 53:1289–97.
Edwards and Gibbs (1994) PCR Meth. Appl., 3:s65–s75.
Bell and Byers (1983) Anal. Biochem., 130:527–35.
Blanquet et al. (1993) Hum. Mol. Genet., 2:975–979.
Uitterlinden et al. (1991) Electrophoresis, 12:119–134.
Uitterlinden et al. (1989) Proc. Natl. Acad. Sci. USA, 86:2742–46.
Poddar and Maniloff (1989) Nucl. Acids Res., 17:2889–2895.
Myers et al. (1987) Methods Enzymol., 155:501–527.
Myers et al. (1985) Nucl. Acids Res., 13:3131–3145.

*Primary Examiner*—W. Gary Jones
*Assistant Examiner*—Amy Atzel
*Attorney, Agent, or Firm*—Rines and Rines

[57] ABSTRACT

An assay for detecting mutations in genes by a two-step multiplex polymerase chain reaction amplification followed by preferably two-dimensional electrophoretic separation of the fragments on the basis of both size and base pair sequence.

18 Claims, 6 Drawing Sheets

METHOD OF AND APPARATUS FOR DIAGNOSTIC DNA TESTING

This is a file-wrapper continuation of application Ser. No. 08/471,249, filed Jun. 6, 1995 now abandoned.

The present invention relates to the diagnostic testing of DNA using polymerase chain reaction (PCR) amplification followed by electrophoretic separation of the resulting fragments to detect possible gene variants of mutational defects and the like; being more particularly directed to new and improved multiplex PCR techniques in combination with preferably two-dimensional electrophoretic separation in denaturing gradient gels.

This invention pertains particularly to tests for the presence of DNA mutations in patients with inherited diseases, including birth defects (e.g. cystic fibrosis) and genetic predispositions to adult chronic diseases (e.g., cancer). More specifically, the invention relates to the quick preparation, by a novel two-step polymerase chain reaction (PCR) amplification, of gene fragments and their subsequent efficient and accurate examination for mutations.

BACKGROUND OF INVENTION

Genes with mutational defects (gene variants or alleles) can be identified by DNA diagnostic testing. Gene variants can be transmitted from parents to children. Some gene variants have a very strong effect and are, by themselves, capable of causing disease. Examples are many mutational variants of the cystic fibrosis transmembrane conductance regulator (CFTR) gene that cause cystic fibrosis. Other gene variants act in combination with gene variants from other loci. Examples include many of the common (polygenic) diseases, like heart disease and cancer. It is possible to test for gene defects in an early stage; that is, in cells from the embryo (pre-natal testing), but also at a much later stage in young, adult or old individuals.

By DNA diagnostic testing, information is obtained about a disease, sometimes before it has become manifest. This greatly facilitates management of the disease, e.g., prevention, treatment. For example, it is possible to test for the presence of particular gene variants in cancers or infectious disease agents in order to predict, e.g., the course of the disease, response to therapy. It is also possible to test individuals for carrying a particular gene variant, which they would not like to see transmitted to their offspring (carrier testing). Finally, it is possible to test individuals at any time (from pre-natal to late age) for inherited gene-encoded predispositions to disease. An example from one end of the spectrum is cystic fibrosis, for which pre-natal testing and carrier screening has already become relatively common. The other end of the spectrum involves late-onset diseases, like cancers and neurodegenerative diseases.

DNA diagnostic testing involves an analysis of the sequence integrity of individual genes. At present, this is costly since accurate testing requires sequencing, or decoding, of the gene, which is labour intensive. Thus far no cost-effective universally applicable standardized system for DNA diagnostics has become available (for a review, see Cotton, 1993, Current methods of mutation detection, Mutat. Res. 285:125–144). In order to be cost-effective and widely accepted a DNA diagnostic system must be accurate (more than 95%), have a high throughput, and not be labour intensive.

GENERAL BACKGROUND OF ANALYSIS TECHNIQUE

It is initially in order briefly to review the general techniques involved in PCR amplification and in electrophoretic separation of fragments, and where the art has applied and is currently applying the same.

A sample of cells, such as derived from blood, is first chemically and physically treated to extract DNA strands carrying genes that occupy only about two percent of the total DNA material in a cell genome, with the remainder of DNA material cluttering up the background. While each cell has two copies of each gene and such can be identified by building blocks or basepairs identified by sequences of letters A, C, G and T as a letter code, they constitute such a small part of the long DNA strands that they must be amplified by making many copies of the same to permit their inspection. This is effected by heat-separating or denaturing of the DNA strand pairs, mixing with appropriate primers to bind or anneal to the beginning and the end of the gene fragments (e.g., gene exons or coding regions) to be investigated, later more fully discussed, and adding sufficient building blocks to generate copies of the gene exons. The successive repeating of this cycle of steps effects a cumulative copying of the exons to produce a purified and amplified quantity—a process generally referred to as the before mentioned polymerase chain reaction or PCR amplification—and more fully reviewed, for example, in Molecular Pathology, Hein and Silverman, Carolina Academic Press, 1994, Chapter 2, Molecular Techniques and Their Automation in the Clinical Laboratory, pages 5–31 (Winn-Deen).

At this stage, it is then in order to inspect or analyze the gene exons to determine if there are mutations from normalcy. This is generally done by electrophoretically separating the DNA purified fragments, preferably on the basis both of size and base-pair sequence, as more fully described by co-applicant Vijg and A. G. Uitterlinden in Two-dimensional DNA typing: A Parallel Approach to Genome Analysis, Ellis Horwood, 1994, particularly at pages 33–40.

Electrophoresis has been used not only for DNA fragment separation but also for separating other substances than genes, such as, for example, for protein analysis, as described in Electrophoresis 1993, 14, 1091–1198. Machines are provided for one-dimensional DNA separation by electrophoresis with fluorescent dye labeling, such as the ABI Prism 377 DNA sequencer of Perkin Elmer; and for two-dimensional DNA typing, as described by co-applicant Vijg and E. Mullaart et al. in Nature, 365, 30 Sep. 1993, Parallel genome analysis by two-dimensional DNA typing, pages 469–471, describing apparatus of Ingeny B. V. of The Netherlands. The first dimension (say horizontal) application of the electric field to an appropriate gel matrix (later discussed) into which the purified DNA fragments have been introduced, causes separation of the fragments by size, larger particles moving slower than smaller particles. By applying the electric field in an orthogonal direction (vertically) with a chemical gradient as of successively more concentrated urea/formamide disposed in the gel, or a temperature gradient established therealong, the DNA fragments will migrate (this time vertically) until they melt and are locked in position in the gel matrix at particular vertical sequence-determined locations. To prevent melting of the entire DNA fragments, the latter can be attached (before the electrophoresis process) to a number of only G's and C's, which are more resistant to melting than A's and T's. This so-called GC-clamping, effectively locks each fragment in position which is determined entirely by the sequence of the exon-part of the fragments. If this sequence is changed at only one position, for example, by the substitution of an AT couple for a GC couple, it will melt later or earlier and hence become locked in a different vertical position than the normal reference fragment.

Such two-dimensional gene scanning (TDGS) has promise for becoming a cost-effective and widely accepted DNA diagnostic system. In this system, as above described, a large number of DNA fragments obtained through polymerase chain reaction (PCR) amplification from a given DNA sample are electrophoretically separated on the basis of both size and basepair sequence. This system is highly accurate (i.e., 99%), since the second dimension separation is based on denaturing gradient gel electrophoresis (DGGE). Indeed, DGGE is the only system with such high accuracy (Sheffield et al., 1993, The sensitivity of single-strand conformation polymorphism analysis for the detection of single base substitutions, Genomics 16, 325–332; Grompe, 1993, The rapid detection of unknown mutations in nucleic acids, Nature Genet. 5, 111–117; Guldberg et al.,1993, Molecular analysis of phenylketonuria in Denmark: 99% of the mutations detected by denaturing gradient gel electrophoresis, Genomics 17, 141–146). Automatic instrumentation for TDGS is partly available and partly under development. TDGS allows the detection of all possible mutations in DNA fragments obtained from one or more genes simultaneously at a high throughput and with a minimum of manual interference.

One major hindrance to the widespread application of TDGS in DNA diagnostics is the difficulty of amplifying many fragments simultaneously in the same reaction tube by PCR (multiplex PCR). In fact, it is often not even possible to find PCR primer sites that amplify the relevant gene fragments and simultaneously fulfil requirements for both PCR and denaturing gradient gel electrophoresis, i.e., optimal PCR reactions and optimal melting behaviour of the amplified fragments. The current procedure begins with amplifying regions of the target DNA, usually the protein-coding regions (exons) of a gene, by PCR. These amplification reactions are conducted separately, e.g., if 27 exons in a gene are being analyzed, then 27 separate PCR reactions must be conducted. In practice, it is usually possible to conduct a few PCR reactions together in one tube (e.g., Edwards and Gibbs, 1994, Multiplex PCR: advantages, development, and application, PCR Methods and Applications 3, S65–S75).

Clearly, with a large number of individuals to be tested and when more than one gene is tested simultaneously in the same TDGS test, the total number of pipetting steps and individual reactions to be carried out can become very high. This increases the labour intensity of the test, but makes it also more complicated with a higher chance of human error. Indeed, in view of this complexity, even complete lab automation where all pipetting steps are done automatically will not solve this problem.

The problem of not being able to PCR-amplify multiple fragments simultaneously under identical reaction conditions in the same tube is an important technical hurdle for TDGS to meet criteria for clinical testing, i.e., laboratory user-friendliness. To reduce the number of PCR reactions via multiplexing, i.e., conducting several PCR amplifications in one reaction by employing multiple sets of primers, is a non-trivial development.

Current approaches for multiplexing are sometimes as simple as combining a few sets of primers for which reaction conditions have been determined separately. However, in most cases multiplex PCRs must be developed with careful consideration for the regions to be amplified, the relative sizes of the fragments, the dynamics of the primers, and the optimization of PCR experimental conditions to accommodate multiple fragments.

A key problem is the positioning of the primers. For gene diagnosis one generally aims at amplifying the exon sequences, splice sites and regulatory regions. Primers for exon-amplifying PCR reactions are ideally placed in intronic sequences adjacent to the exons. This provides some margin for adjustment of fragment length or amplification quality as well as information about mutations affecting splice sites. These are the first limits to primer choice.

Then, primers should be positioned so that non-specific amplification at other sites than the target sequences does not occur. Indeed, the human genome is $3\times10^9$ basepairs long, which provides ample opportunity for fortuitous sequence homology between the target and other non-target sequences. This problem is not typical for multiplexing, but can also occur when one wishes to amplify only one fragment at a time. This is the second limitation to primer choice.

For multiplexing, primers should be selected so that their predicted hybridization kinetics are similar to those of other primers in the multiplex reaction. This is a third limitation to primer choice. These limitations to primer choice, with total genomic DNA as template, are the reasons why multiplex groups are usually small (typically less than 5 fragments).

For optimal separation in TDGS there is a fourth formidable limit to primer choice. TDGS requires DNA fragments of 100–600 bp on average. One of the two primers should be coupled to a GC-rich fragment to provide for a GC-clamp as highest melting domain in the fragment to be generated by PCR. This is essential to guarantee the highest sensitivity to detect mutations in the second (denaturing gradient) dimension gel (Myers et al., 1985, Nearly all single base substitutions in DNA fragments joined to a GC-clamp can be detected by denaturing gradient gel electrophoresis, Nucl. Acids Res. 13, 3131–3145; Myers, et al., 1987, Detection and localization of single base changes by denaturing gradient gel electrophoresis, Meth. Enzymol., 155, 501–527). Primers should then be positioned in such a way that the target fragment comprises only one single domain, that melts earlier (at lower urea/formamide concentration or temperature) than the GC-clamp attached to it. It turned out that optimal PCR conditions for both PCR (let alone multiplexing) and optimal melting profiles are difficult, if not impossible, to realize (e.g., compare the RB DGGE design by Blanquet et al., 1993, Identification of germline mutations in the RB1 gene by denaturant gradient gel electrophoresis and polymerase chain reaction direct sequencing, Hum. Molec. Genet. 2, 975–979, with our present design).

The present invention involves a combination of so-called long-PCR with short-PCR. Recently, PCR amplification methods were developed allowing the amplification of large fragments (up to 40 kb) from the genomic DNA. We have taken advantage of this development by using long-PCR to first amplify all the coding regions of the target gene(s) in the smallest number of fragments possible. Using these long non-overlapping amplicons as template we then PCR-amplify the small fragments, required for the TDGS, in a multiplex format. In this way the target sequence is first amplified away from the contaminating genomic DNA, which allows to obtain the small PCR fragments under identical conditions from this pre-purified template.

Using the above procedure, primer sets selected only on the basis of optimal melting behaviour of the PCR amplicons, also exhibited optimal behaviour in the PCR and even allowed extensive multiplexing. In part this phenomenon can be ascribed to the pre-purification by the long-PCR. Indeed, the long-PCR greatly increases the amounts of target sequence relative to other genomic DNA sequences, thereby greatly decreasing complexity of the reaction and increasing its specificity.

Although the above described phenomenon can be explained by the reduction of complexity through the preparation of a purified template, an exact explanation can not be given. Indeed, the sheer magnitude of the effect is surprising and necessitates a reevaluation of the factors involved in PCR optimization. One thing is clear, however. The present invention alone enables one to design and perform an efficient TDGS test, because primers can now be selected on the basis of melting profile alone and multiplexing is greatly facilitated.

The invention is also generally applicable. Indeed, selection of primers in every PCR-based diagnostic reaction is an important issue and many potential priming sites turn out to give poor results. Multiplexing then generates additional problems, which is the reason that it is not widely used. The long-PCR/short-PCR two-step amplification system offers an immediate and simple solution to this problem.

OBJECTS OF INVENTION

An object of the invention, accordingly, is to provide a new and improved method and apparatus for diagnostic DNA testing that obviate the above described difficulties.

A further object is to provide for novel detection of mutations in genes by a two-step multiplex polymerase chain reaction amplification using long and short multiplex PCR followed by two-dimensional electrophoretic separation of the fragments on the basis of both size and basepair sequence.

Other objects will be explained hereinafter and pointed out in connection with the appended claims.

BRIEF DESCRIPTION OF THE FIGURES

The invention will now be described in connection with the accompanying drawings in which.

SUMMARY OF THE INVENTION

In summary, in an important aspect, the invention embraces a method of analyzing predetermined gene exons derived from DNA, that comprises, adding primer pairs to successive groups of the gene exons followed by effecting polymerase chain reaction amplifications thereof in a common tube, as a first step and relatively long multiplex polymerase chain reaction; adding further primer pairs to each of the gene exons and effecting polymerase chain reaction amplifications thereof in the common tube as a second step and short multiplex polymerase chain reaction; and electrophoretically separating the gene fragments.

Preferred and best mode techniques will now be described.

DESCRIPTION OF PREFERRED EMBODIMENTS

The present invention, as before stated, involves the design of an accurate and efficient mutation detection test on the basis of a minimal number of two-step multiplex PCR reactions in combination with automatic two-dimensional separation of the fragments to detect all possible mutations in the gene(s) simultaneously.

Table 1 lists the different steps in the design of a TDGS test, with the RB (retinoblastoma) tumor suppressor gene as a model. First, the gene sequences are retrieved from a database (e.g. Genbank) and the target regions, i.e., exons, splice sites, regulatory regions, are defined. Then, primers are positioned to obtain all target regions as the smallest possible number of fragments that can still be amplified through long-PCR, i.e. up to at least 20 kb (TaKaRa LA PCR Kit. Product Insert). Some general guidelines in choosing primer sequences for long-PCR have been described (Foord and Rose, 1994, Long-distance PCR, PCR Methods and Applications 3, S149–S161), but empirical determination of optimal primers remains necessary.

TABLE 1

Design of a TDGS test.

1. Retrieve sequence from database.
2. Position primers for long-PCR to cover all desired regions (e.g., coding sequences, splice sites, regulatory regions, mutation hotspots) by the smallest possible number of amplicons.
3. Position primers for short-PCR according to the following criteria:
   a. the desired target sequences should be covered by amplicons of between 100 and 600 bp
   b. amplicons should have optimal melting behaviour, i.e., consist of one lowest-melting domain in addition to the GC-clamp attached to one of the primers.
   c. optimal amplicon distribution over the 2-D gel
   d. similar reaction kinetics
4. Set up PCR conditions separately for each primer set with the long-PCR products as template.
5. Develop multiplex co-amplification conditions by grouping primer sets and adjusting reaction components.

Figure 2A:
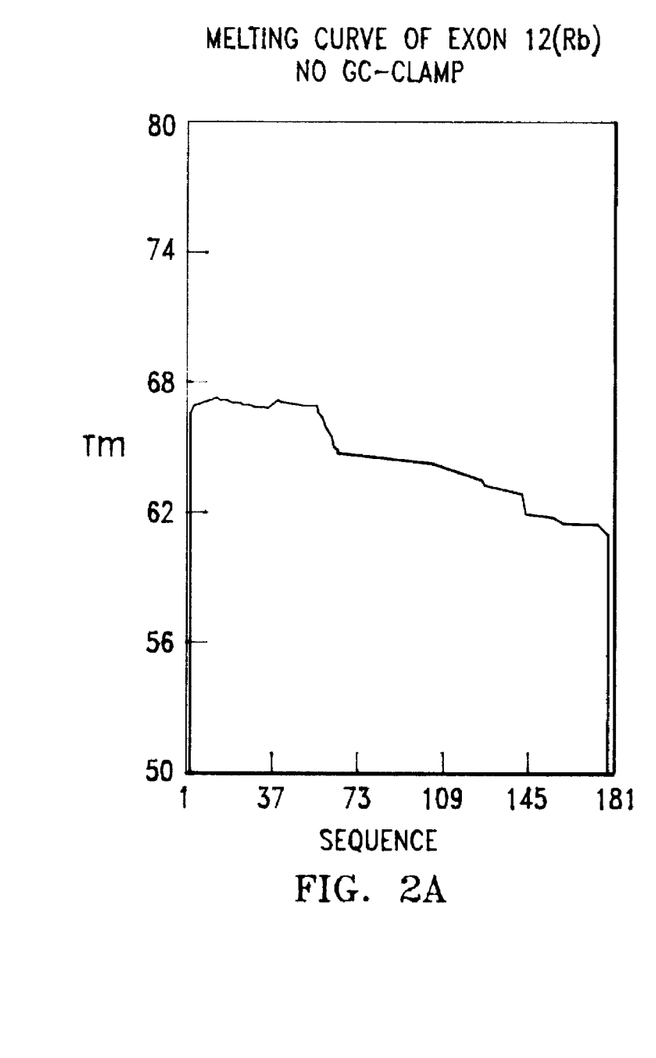
FIGS. 2A and 2B show the melting curves for RB exon 12 with and without the GC-clamp, (i.e. retinal blastoma gene).
Figure 2B:
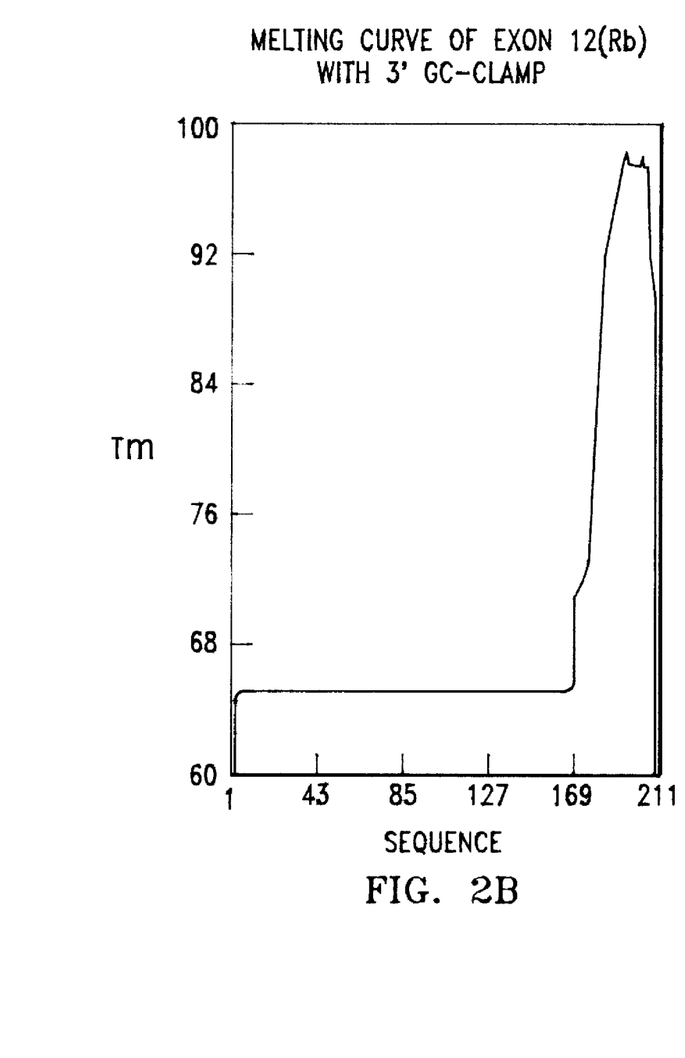

As listed in Table 1, item 3, then, using the long-PCR fragments as template, primers for short-PCR are selected to yield fragments of between 100 and 600 bp. The main selection criterion here is necessarily the melting behaviour of the fragments. In the ideal situation, each amplicon should comprise only one melting domain, which should be lower (less stable) than the GC-clamp attached to it. Attachment of a 30–40 bp GC-clamp is accomplished by making it part of one of the primers (Sheffield et al., 1989, The sensitivity of single-strand conformation polymorphism analysis for the detection of single base substitutions, Genomics 16, 325–332). Optimal melting behaviour is determined of each candidate target sequence by using a computer program (e.g., MELT87; Lerman and Silverstein, 1987, Computational simulation of DNA melting and its application to denaturing gradient gel electrophoresis, Meth. Enzymol. 155, 482–501). An example of an amplicon with optimized melting behaviour through GC-clamping is shown in FIGS. 2A and 2B, in connection with exon 12 for RB.

In general, a collection of primers is selected that allows an optimal distribution, in both size and DGGE dimension, over the 2-D gel. Due to the high resolution of 2-D gels (5–10-bp size differences are easily resolved) this is generally not too difficult. With 50 fragments or less, spot distribution is hardly an issue and primers can simply be selected according to their melting behaviour.

Figure 3:
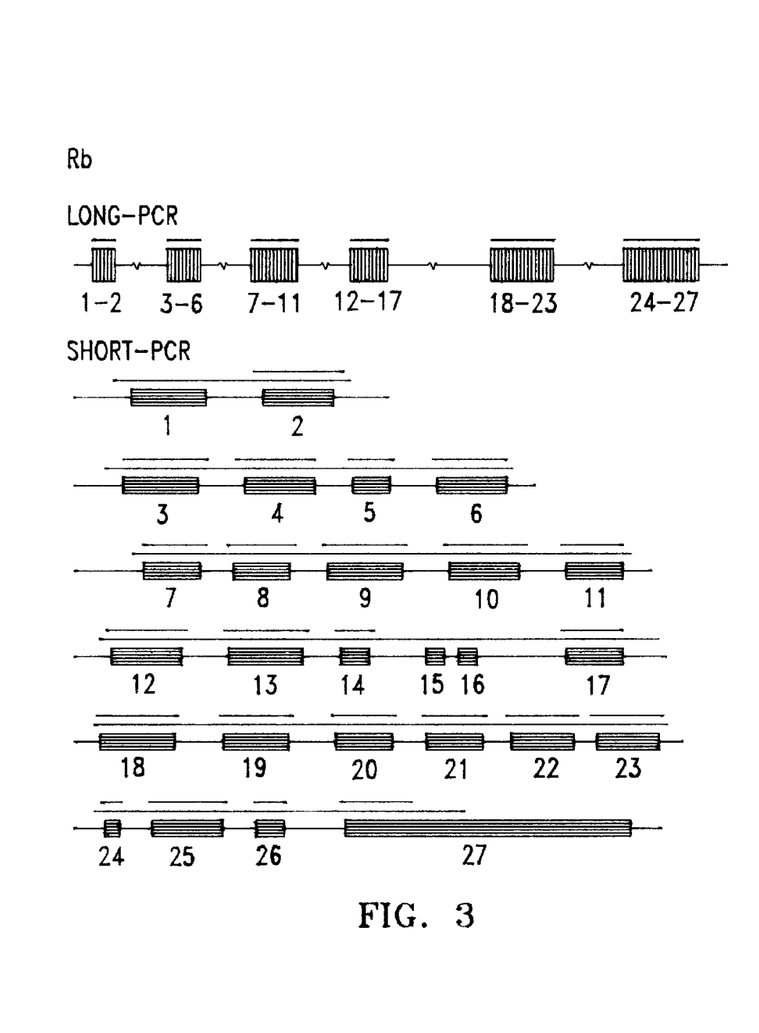
FIG. 3 shows maps of the tumor suppressor gene RB indicating the positions of the PCR primers for the long- and short-PCR reactions.

FIG. 3 shows the collection of amplicons selected for the RB gene, together with the non-overlapping long-PCR fragments that served as templates. Together the short-PCR fragments represent more than 90% of the RB coding region.

Figure 4:
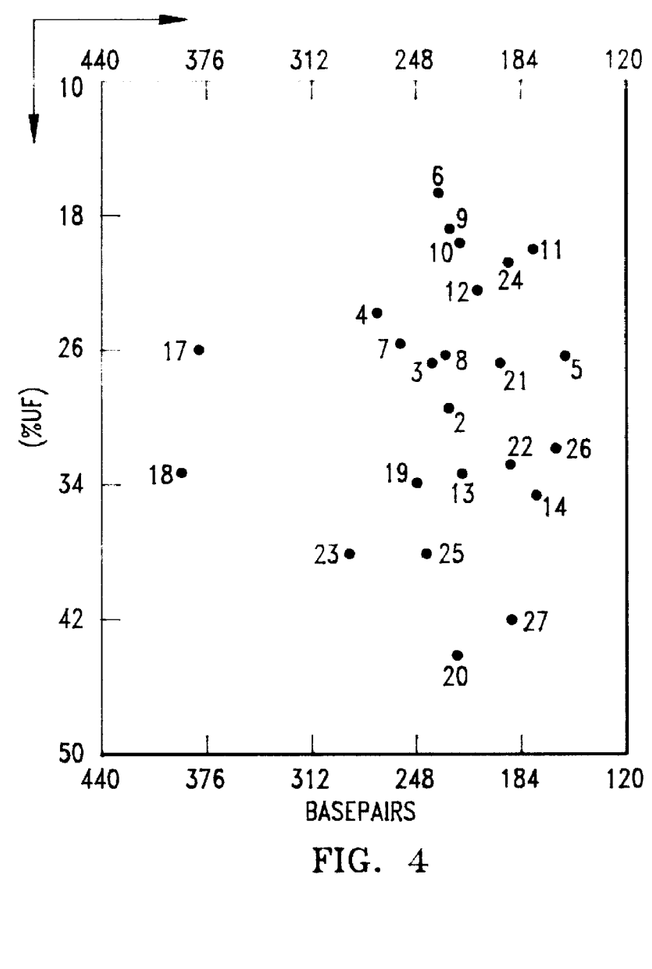
FIG. 4 shows a computer print with the predicted positions of the short-PCR fragments in a 2-D gel electrophoresis pattern with the indicated specifications.
Figure 5:
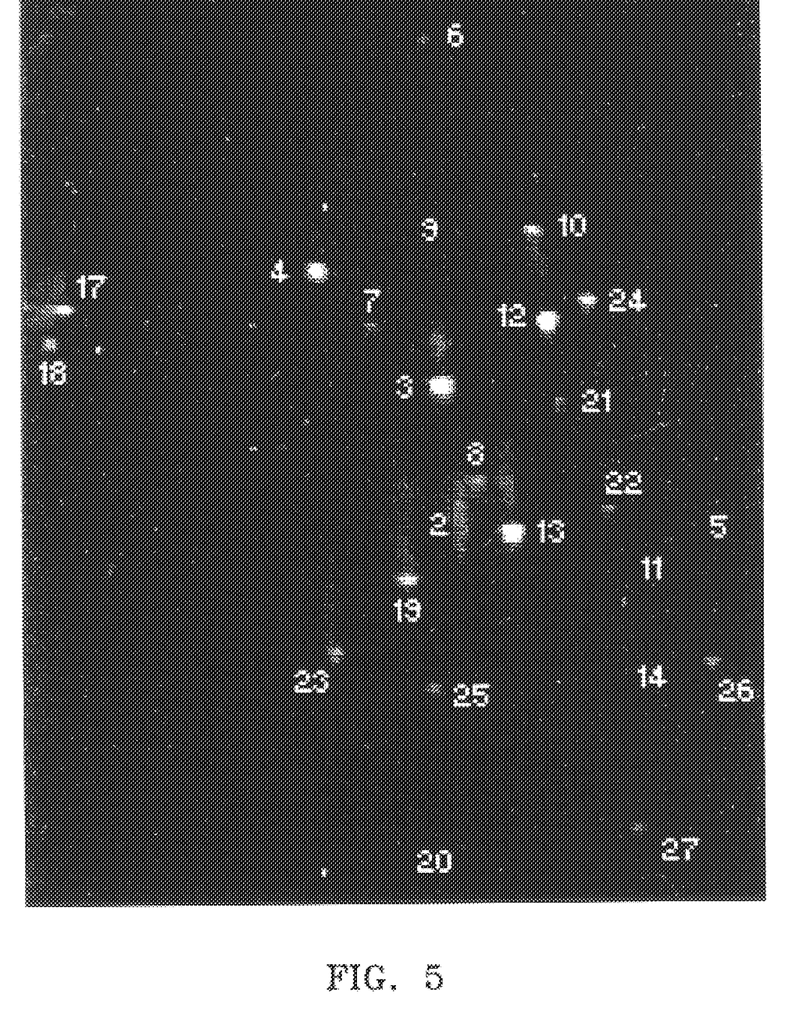
FIG. 5 shows the actual gel separation pattern indicating correspondence with the theoretically predicted pattern.

FIGS. 4 and 5 show the theoretical and the empirical spot distribution for the 24 exons of the RB gene covered by the amplicons shown in FIG. 3. Although there are differences, most notably the spot representing exon 11, our conclusion is that overall the melting program accurately predicts spot positions.

It is important to realize that without the first long-PCR step, the optimal melting criterion is usually in conflict with other primer design criteria applied to PCR with total genomic DNA as template. Indeed, for the RB gene it was found to be impossible to select conditions suitable for both optimal separation in DGGE and optimal priming in PCR. The pre-purification step represented by the long-PCR is apparently a conditio sine qua non for the design of an optimal set of PCR primers in TDGS.

Figure 6:
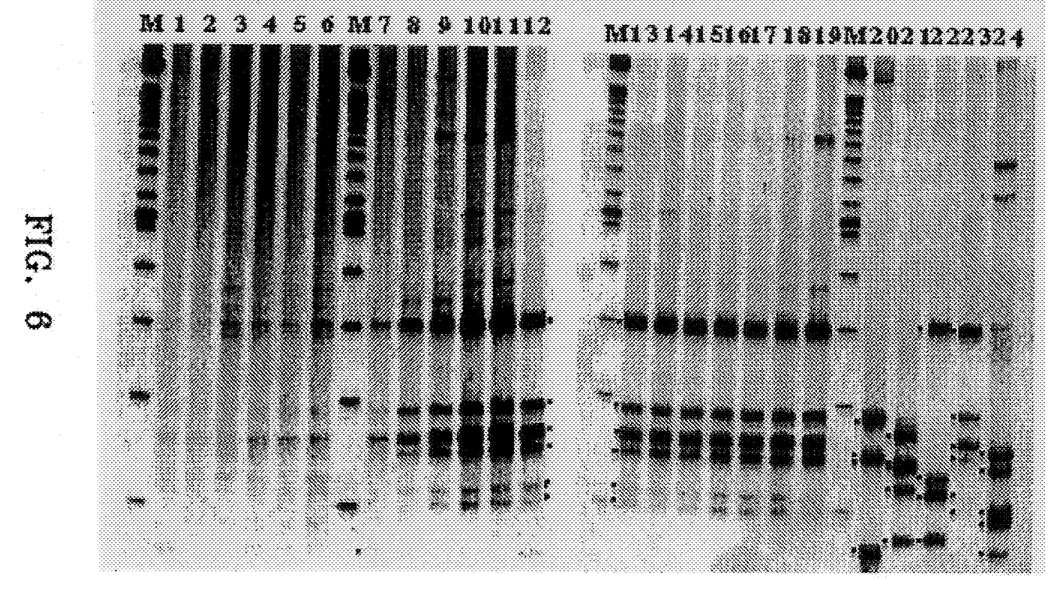
FIG. 6 shows that with the long-PCR product for exons 18–23 as template all 6 of the short PCR fragments are obtained (lanes 7–12), whereas with total genomic DNA as template most products are missing (lanes 1–6). It also shows that only 5 ng total genomic DNA is sufficient as starting material for the long-PCR (lane 13), and that all short PCR products are obtained with the long-PCR products as template (lanes 20–24).

When the test format is established, the two-step PCR amplifications are carried out in a multiplex format. It is the possibility to design and perform multiplex PCR reactions that represents the core of the present invention. The necessity of the first, long-PCR step for a successful multiplex PCR is demonstrated by the results shown in FIG. 6. In FIG. 6, the 6 lanes on the left contain PCR products obtained after performing a multiplex PCR of exons 18–23 (6 fragments) of the RB gene, using different amounts of total genomic DNA as template. Clearly, virtually no products of the desired lengths are obtained. The latter is in contrast to lanes 7–12, in which the products were applied of the same multiplex PCR reaction, but this time with the long-PCR product as template. The long-PCR was performed at different cycles and it is clear that only 5–10 cycles are needed to generate enough template for a successful multiplex PCR.

Lanes 13 to 19 contain the multiplex short-PCR products obtained with the long-PCR products as template, at different amounts of starting material, i.e., different amounts of total genomic DNA used in the long-PCR reaction. Interestingly, 5 ng total genomic DNA is sufficient to obtain all the products. Since clinical material is sometimes not available in plentiful amounts (e.g., breast cancer needle biopsies) this is an important result, indicating that a successful test can be performed with very small amounts of DNA.

Finally, lanes 20–24 of FIG. 6 contain the products of the 5 multiplex PCRs corresponding to the 6 long-PCR sets (long-PCR groups 1 and 6 were combined; see also FIG. 3 and later discussed Table 2). Further adjustments of PCR conditions and/or primers should make it possible to obtain an even smaller number of multiplex sets for this gene. The there is no reason why the entire RB gene coding region couldn't be amplified in only one single PCR reaction. After the second PCR, the fragments are allowed to undergo one complete round of denaturation/renaturation to facilitate the formation of heteroduplexes. There are presented in Table 2, a listing of the primer pairs for TDGS for the case of RB; the exon numbers being listed in the left most table, with long PCR primer codes for six exon groups (0 through 24–27) and short PCR primers for the individual 27 exons.

Figure 1:
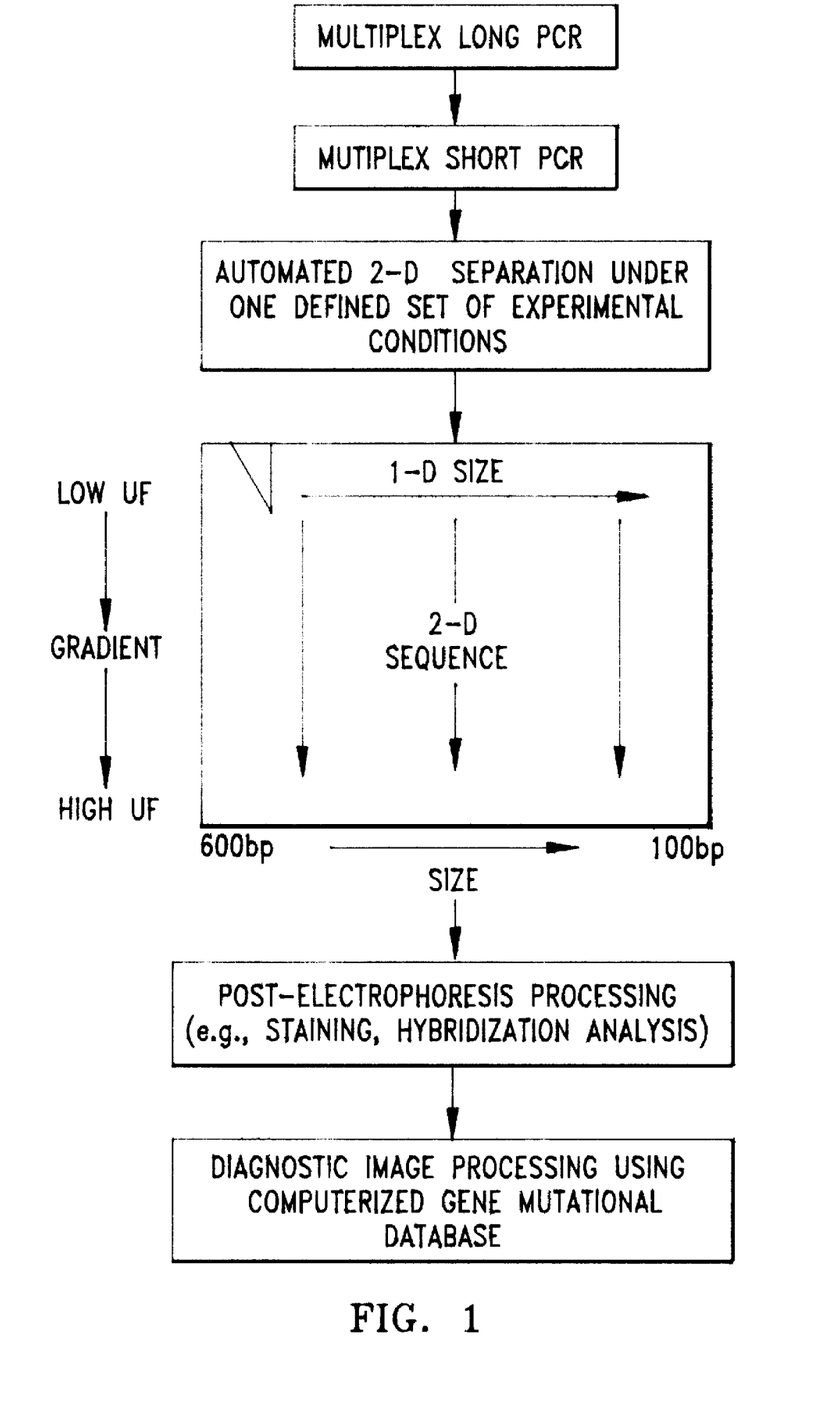
FIG. 1 illustrates the sequence of process steps for performing the invention.

Subsequent to the PCR, the mixture of fragments is subjected to 2-D electrophoresis in a denaturing gradient gel (FIG. 1). The availability of an automated instrument greatly simplifies this process. The instrument used here allows 10 gels at a time to run without manual interference, i.e., cutting out lanes and loading these onto a second gel. All experiments involving optimization of the experimental conditions were carried out using manual instruments. After 2-D electrophoresis the gels are released from between the glass plates and stained with ethidium bromide or any other stain.

TABLE 2

Primer pairs for TDGS of RG

RB: Long-PCR

| exons | primers 5' - 3' | size |
|---|---|---|
| 0–2 | TGTCAGGCCTGCCTGACAGACTTCTATTCAGCA ATGTTAGCAGAGGTAAATTTCCTCTGGGTAATGG | 4.5 kb |
| 3–6 | GCAGTCATTTCCCAACACCTCCCCTCTGT AAGCCAAGCAGAGAATGAGGGAGGAGTACATTAC | 9 kb |
| 7–11 | TCAGCAGTTTCTCCCTCCAAGTCAGAGAGGC GAGACCAGAAGGAGCAAGATCAGGTAGTAG | 10 kb |
| 12–17 | ACCATTCCCCCTACTCTCCATGGTCCATG CTCACAGGAAAAATACACAGTATCCTGTTTGTGTGGC | 12.4 kb |
| 18–23 | CCAGCCTTGCATTCTGGGGATGAAGC AGTCGTAAATAGATTTTCTTCACCCCGCCCC | 14 kb |
| 24–27 | GCCTTTGCCCTCCCTAAATATGGGCAATGG CTGGGTTATCAGGACTCCCACTCTAGGGCC | 7.3 kb |

RB: Short-PCR

| exon | primers 5' - 3' | size | Tm (% UF) | multiplex set |
|---|---|---|---|---|
| 2 | [GC1]TTGATTTATAAGTATATGCCA CAAAACGTTTTAAGAAAATCC | 229 bp | 30 | E |
| 3 | [GC1]CCAGTGTGTGAATTATTTAA | 239 bp | 27 | A |

TABLE 2-continued

Primer pairs for TDGS of RG

|   |   |   |   |   |
|---|---|---|---|---|
|   | CCTTTTATGGCAGAGGCTTATA | | | |
| 4 | [GC1]GAATTGAAATATCTATGATT | 270 bp | 24 | A |
|   | ATCAGAGTGTAACCCTAATA | | | |
| 5 | [GC1]TACTATGACTTCTAAATTACG | 157 bp | 27 | A |
|   | GTGAAAAATAACATTCTGTG | | | |
| 6 | TGGAAAACTTTCTTTCAGTG | 237 bp | 17 | A |
|   | [GC1]GAATTAGTCCAAAGGAATGC | | | |
| 7 | [GC1]CCTGCGATTTTCTCTCATAC | 257 bp | 26 | B |
|   | GCAACTGCTGAATGAGAAAG | | | |
| 8 | GTTCTTATCTAATTTACCACT | 229 bp | 27 | B |
|   | [GC1]TTTTAAAGAAATCATGAAGTT | | | |
| 9 | [GC1]AGTCAAGAGATTAGATTTTG | 227 bp | 20 | B |
|   | ATCCTCCCTCCACAGTC | | | |
| 10 | [GC1]GACATGTAAAGGATAATTGT | 222 bp | 21 | B |
|   | GCAAATCAATCAAATATACC | | | |
| 11 | AGTATGTGAATGACTTCACT | 174 bp | 21 | B |
|   | [GC1]TATAATATAATTAAAAGTAGG | | | |
| 12 | CTCCCTTCATTGCTTAACAC | 211 bp | 24 | C |
|   | [GC1]TTTCTTTGCCAAGATATTAC | | | |
| 13 | [GC1]GATTACACAGTATCCTCGAC | 224 bp | 34 | C |
|   | GCAGTACCACGAATTACAATG | | | |
| 14 | [GC1]GTGATTTTCTAAAATAGCAGG | 179 bp | 35 | C |
|   | ACCGCGCCCGGCTGAAAT | | | |
| 17 | [GC1]TTCTTTGTCTGATAATAAC | 380 bp | 26 | C |
|   | CTCTCACTAACAATAATTTGTT | | | |
| 18 | [GC1]GACTTTTAAATTGCCACTGT | 393 bp | 33 | D |
|   | ATTCCCTACAGTTTCTTTAT | | | |
| 19 | [GC1]CAACTTGAAATGAAGAC | 248 bp | 34 | D |
|   | CGTCCCGCTGCTCTTGAAAATAATCATC | | | |
| 20 | [GC1]AAAATGACTAATTTTTCTTATTCCC | 227 bp | 44 | D |
|   | AGGAGAGAAGGTGAAGTGC | | | |
| 21 | [GC2]CATTCTGACTACTTTTACATC | 201 bp | 28 | D |
|   | CGGGCTTACTATGGAAAATTAC | | | |
| 22 | [GC3]CTTTTTACTGTTCTTCC | 194 bp | 33 | D |
|   | CCAATCAAAGGATACTTTTG | | | |
| 23 | [GC1]TCTAATGTAATGGGTCCACC | 281 bp | 38 | D |
|   | CCCTACTTCCCTAAAGAGAAAAC | | | |
| 24 | CGGAATGATGTATTTATGCTCA | 195 bp | 22 | E |
|   | [GC1]TTCTTTTATACTTACAATGC | | | |
| 25 | [GC1]ATGATTTAAAGTAAAGAATTCT | 245 bp | 38 | E |
|   | CATCTCAGCTACTGGAAAAC | | | |
| 26 | [GC1]TCCATTTATAAATACACATG | 161 bp | 32 | E |
|   | ATTTCGTTTACACAAGGTG | | | |
| 27 | [GC1]TACCCAGTACCATCAATGC | 191 bp | 43 | E |
|   | TCCAGAGGTGTACACAGTG | | | |

GC-clamps:
GC1: CGCCCGCCGCGCCCCGCGCCCGTCCCGCCC (30 mer)
GC2: CGCCCCGCGCCGCCGCCCCGCCCCCGCCCGTCCCGCCC (38 mer)
GC3: CGCCCCGCCGCGCCCCGCGCGCCCGGTCCCCGCGC (35 mer)

Figure 7:
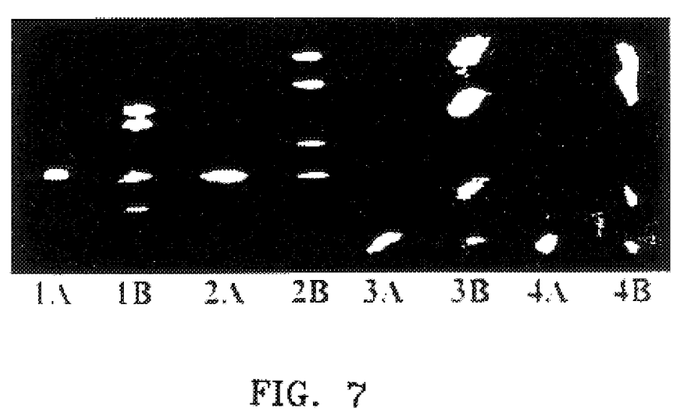
FIG. 7 shows details of wildtype (homozygous normal) fragments and several heterozygous mutants.

The resulting patterns were documented and evaluated (by eye and image analysis) for the occurrence of mutations. Under the conditions applied, i.e., GC-clamping and heteroduplexing, heterozygous mutations result in 4 spots: the 2 homoduplex variants and the 2 heteroduplex variants (illustrated in FIG. 7). The latter are not always separated. Since mutations may also occur in a homozygous state it can be necessary to mix each sample before PCR with a control sample to make sure that heteroduplex molecules will be present.

The following provides details of the manner in which the embodiments of the present invention may be made and used in order to achieve the accurate and efficient preparation and examination of gene fragments in DNA diagnostic testing. This description, which is focused on an illustrative or model gene, i.e., the tumor suppressor gene RB previously discussed, is not to be construed as specifically limiting the invention. The same procedure may be used on other genes and/or to combine even more PCR fragments in the same tube, within the purview of one skilled in the art, and are to be considered to fall within the scope of this invention.

A. Design of the RB Two-Step PCR TDGS Test

Sequence Retrieval. The sequence of the RB gene is retrieved from a database, i.e., Genbank. The target regions, i.e., exons, splice sites, regulatory regions are defined.

Primer Selection for multiplex Long-PCR. Primer pairs for long-PCR are positioned in such a way as to cover all target regions by the smallest possible number of fragments that can still be amplified through long-PCR. Long-PCR primers are also selected for highest specificity, optimal annealing temperature and minimal self-complementation for multiplex long-PCR, e.g., by using primer design software. The design of the long-PCR multiplex is relatively easy in view of the ample positioning space of the primers.

Primer Selection for Multiplex Short-PCR. Primer pairs for short-PCR are selected on the basis of the following criteria:

a. the desired target sequences should be covered by amplicons of between 100 and 600 bp
b. amplicons should have optimal melting behaviour, i.e., consist of one lowest-melting domain in addition to the GC-clamp attached to one of the primers.

c. optimal amplicon distribution over the 2-D gel
d. similar reaction kinetics

Criterion b, above; is frequently in conflict with standard primer design criteria, if applied on total genomic DNA. The present invention proved to be both necessary and sufficient for the design and performance of TDGS as a rapid, accurate and practical tool for mutation detection in the RB gene.

Multiplex groups are selected empirically on the basis of the behaviour of the primers in various multiplex reactions. For RB multiplex groups were made according to the long-PCR. That is, all short PCRs with one long-PCR fragment as template were amplified together as one multiplex group. Two long-PCR groups were actually combined as one multiplex group. All short-PCR fragment may also be amplified together. As before explained, Table 2 lists the primer pairs used for the long and short PCRs, fragment sizes, annealing temperatures, melting temperatures and the five different multiplex groups.

B. PCR Reactions and Heteroduplexing

Primers (deprotected and desalted) can be obtained from various sources. Our primers were obtained from Gibco BRL. For long-term storage, primers should be kept, for example in a stock solution of 100 $\mu$M in ultrapure water, at $-20°$ C. For short-term use, we kept them at $-20°$ C. as a solution of 12.5 $\mu$M in ultrapure water.

We carried out our PCR reactions in thermowell tubes (Costar, Cambridge, Mass.) in a GeneE thermocycler (Techne, Cambridge, UK) fitted with a Heated Lid, removing the need for an oil overlay on the samples. Multiplex long PCR reactions (6 fragments) were carried out in a 100 $\mu$l volume with 5–500 ng genomic DNA as template and 0.2 $\mu$M of each primer, using the LA PCR kit (TaKaRa). PCR reactions are performed according to the manufacturer's instructions. The conditions were as follows. First, one cycle of 94° C., 1 min, followed by 30 cycles of 98° C., 20 sec/68° C., 12 min with 10 s increment per cycle, and finally one cycle of 72° C., 12 min. The PCR products are stored at $-20°$ C. for further use.

Short PCR reactions are carried out, using the same GeneE thermocycler, in a 50 $\mu$l volume with 2 $\mu$l long-PCR product, 0.2–0.5 $\mu$M of each primer, 0.25 mM dNTPs, 2.5–4.5 mM MgCl$_2$, 3 units of Taq polymerase (Gibco BRL or Promega). The PCR conditions are as follows. One cycle of 94° C., 2 min, then 30 cycles of 94° C., 40 sec/41° C., 40 sec/69° C., 2 min (with a 2-sec increment increase per cycle) and finally one cycle of 72° C., 10 min.

After the short PCR, fragments are heteroduplexed by one complete round of denaturation/renaturation. That is, 98° C., 10 min/55° C., 30 min/41° C., 30 min.

After PCR and heteroduplexing the contents of the tubes are mixed and $\frac{1}{10}$ volume of loading buffer is added. Based on ethidium bromide staining, there is usually enough sample for several runs. When the total volume is too large for the slot capacity, the sample (prior to adding loading buffer) has to be ethanol-precipitated and re-dissolved in a smaller volume.

C. Two-Dimensional Electrophoresis.

Instruments for both manual and automatic 2-D electrophoresis were from the before mentioned Ingeny B. V. (Leiden, The Netherlands). For manual electrophoresis, the mixtures of DNA fragments were first subjected to size separation using a 0.75 mm thick 9% PAA gel at 45° C. for 5–6 h. The separation pattern was visualized by ethidium bromide staining for 10 min and UV transillumination of the gel, which lies on a glass plate to protect the DNA fragments from damage by the UV light. The 100 to 600 bp region in the middle part of the lane (so not including the edges) was quickly cut out and applied to a 1-mm thick 9% PAA gel containing a 0–60% (RB) or 30–90% (p53) urea/formamide (UF) gradient. Gradients were poured using a simple gradient former (Gibco BRL). Electrophoresis was for 7.5–11 h at 60° C. and 200 V. After electrophoresis, the gels were stained with 0.5 $\mu$g/ml ethidium bromide for 15–20 min and destained in water for another 15 min. The patterns were documented under UV illumination using a polaroid camera.

For automatic 2-D electrophoresis, gels were poured, ten at a time, in the gel-casting device that comes with the automated 2-D electrophoresis instrument according to the manufacturer's instructions (Ingeny B. V., Leiden, The Netherlands). After polymerization, the gels (between glass plates) are removed from the gel-casting box and cleaned with a wet tissue. They are then placed in the instrument according to the manufacturer's instructions, that is, in two gel-holding cassettes with silicone-side sealings. The instrument containing buffer heated to 45° C. is put in the 1-D mode with the power switched off. After adding loading buffer, samples (up to 40 $\mu$l) are loaded in the V-shaped wells of the gels in the automated 2-D electrophoresis instrument. Gels of 9% acrylamide, 0.25 % TAE were used with a gradient of 0–60% urea/formamide. The first dimension was run at 180 V for 4 h at 45° C. The second dimension was run at 200 V for 7.5–11 h at 60° C. After electrophoresis the gels were stained with ethidium bromide and the patterns documented under UV illumination as described for the manual instruments.

In summary, while the present invention is described in connection with two-step (long and short) multiplex polymerase chain reaction amplifications followed by two-dimensional electrophoretic separation, such is also useful with one-dimensional electrophoresis or with other methods for mutation detection that require PCR-amplified target sequences.

Further modifications will also occur to those skilled in this art and such are considered to fall within the spirit and scope of the invention as defined in the appended claims.

What is claimed is:

1. A method of analyzing predetermined gene exons derived from DNA, that comprises, adding multiple primer pairs to successive groups of the gene exons followed by effecting multiplex long-distance polymerase chain reaction amplifications thereof in a common container to achieve non-overlapping resulting amplicons in the range of about 4.5 to 40 kb; adding further primer pairs to each of the gene exons and then effecting multiplex polymerase chain reaction amplifications thereof in the same common container to achieve resulting amplicons in the range of about 100–600 bp; and electrophoretically separating the resulting amplicons.

2. The method as claimed in claim 1, wherein the electrophoretic separation is on the basis of size along one dimension.

3. The method as claimed in claim 2, wherein the electrophoretic separation further comprises electrophoretic separation along a temperature gradient or chemical denaturing gradient in an orthogonal dimension to distribute the gene fragments at particular sequence locations along the orthogonal dimension; and comparing such locations with those of normal gene fragments to detect genetic mutations.

4. The method as claimed in claim 3, wherein the primers are oligonucleotide primers labelled with fluorescent dyes.

5. The method as claimed in claim 3, wherein the nucleotides used in the polymerase chain reaction are fluorescently labelled.

6. The method as claimed in claim 3, wherein the electrophoretic separation is performed in a chemical denaturing gradient gel.

7. The method as claimed in claim 6, wherein the chemical gradient is a urea/formamide gradient.

8. A method of analyzing predetermined gene exons derived from DNA, that comprises, adding multiple primer pairs to successive groups of the gene exons followed by effecting multiplex long-distance polymerase chain reaction amplifications thereof in a common container to achieve non-overlapping resulting amplicons in the range of 4.5–40 kb; adding GC clamped primer pairs to each of the gene exons and then effecting multiplex polymerase chain reaction amplifications thereof in the same common container to achieve resulting amplicons in the range of 100–600 bp; and electrophoretically separating the resulting amplicons, wherein the electrophoretic separation is a two dimensional separation, and wherein one dimension separates on the basis of size and the orthogonal dimension is performed in a gel where a temperature gradient is applied, so as to distribute the resulting amplicons at particular sequence locations along the orthogonal dimension; and comparing said locations to those of resulting amplicons of normal genes to detect genetic mutations.

9. The method as claimed in claim 3, wherein said gene is the retinoblastoma gene and the retinoblastoma gene exon groups for multiplex long-distance polymerase chain reaction are exons 1–2, exons 3–6, exons 7–11, exons 12–17, exons 18–23, and exons 24–27.

10. A method of analyzing predetermined gene exons derived from DNA, that comprises, adding multiple primer pairs to successive groups of the gene exons followed by effecting multiplex long-distance polymerase chain reaction amplifications thereof in a common container to achieve non-overlapping resulting amplicons in the range of about 4.5 to 40 kb; and adding further primer pairs to each of the gene exons and then effecting multiplex polymerase chain reaction amplifications thereof in the same common container to achieve resulting amplicons in the range of about 100–600 bp.

11. A method of analyzing predetermined gene exons derived from DNA, that comprises, adding multiple primer pairs to successive groups of the gene exons followed by effecting multiplex long-distance polymerase chain reaction amplifications thereof in a common container to achieve non-overlapping resulting amplicons in the range of 4.5–40 kb; adding GC clamped primer pairs to each of the gene exons and then effecting multiplex polymerase chain reaction amplifications thereof in the same common container to achieve resulting amplicons in the range of 100–600 bp, to co-amplify as many mutational gene exons as possible in a manner suitable for denaturing gradient electrophoretic analysis; and thereupon electrophoretically separating the gene fragments.

12. A method of analyzing predetermined gene exons derived from DNA, that comprises adding multiple primer pairs to successive groups of the gene exons followed by effecting multiplex long-distance polymerase chain reaction amplifications thereof in a common container to achieve non-overlapping relatively long resulting amplicons in the range of 4.5–40 kb and to increase the number of gene exons that can be amplified simultaneously in one multiplex polymerase chain reaction; adding GC-clamped primer pairs to each of the gene exons and then effecting multiplex polymerase chain reaction amplifications thereof in the same common container with to achieve resulting amplicons in the range of 100– 600 bp; and thereupon electrophoretically separating the resulting amplicons; and in which the electrophoretic separation is effected in a gel and in which a temperature gradient is applied in the gel.

13. A method of analyzing predetermined gene exons derived from DNA that comprises adding multiple primer pairs to successive groups of the gene exons followed by effecting multiplex long-distance polymerase chain reaction amplifications thereof in a common container to achieve non-overlapping resulting amplicons in the range of 4.5–40 kb; adding further primer pairs to each of the gene exons and then effecting multiplex polymerase chain reaction amplifications thereof in the same common container with to achieve resulting amplicons in the range of 100–600 bp; electrophoretically separating the resulting amplicons and in which the electrophoretic separation is effected in a gel in which a temperature gradient is applied in the gel.

14. A method of analyzing predetermined gene exons derived from DNA that comprises adding multiple primer pairs to successive groups of the gene exons followed by effecting multiplex long-distance polymerase chain reaction amplifications thereof in a common container to achieve non-overlapping resulting amplicons in the range of 4.5–40 kb; adding GC-clamped primer pairs to each of the gene exons and then effecting multiplex polymerase chain reaction amplifications thereof in the same common container with to achieve resulting amplicons in the range of 100–600 bp; and thereupon electrophoretically separating the resulting amplicons, wherein electrophoretic separation is effected along a first dimension followed by separation along a dimension orthogonal to the first dimension wherein the orthogonal dimension comprises a temperature gradient or a chemical denaturing gradient to distribute the resulting amplicons at particular sequence locations along the orthogonal dimension.

15. The method as claimed in claim 11, wherein the primers are oligonucleotide primers labeled with fluorescent dyes.

16. The method as claimed in claim 11, wherein the polymerase chain reactions employ fluorescently labeled nucleotides.

17. The method as claimed in claim 8, wherein a gradient of urea and formamide is applied in the gel.

18. The method as claimed in claim 8, wherein said gene is the retinoblastoma gene and the retinoblastoma gene exon groups for multiplex long-distance polymerase chain reaction are exons 1–2, exons 3–6, exons 7–11, exons 12–17, exons 18–23, and exons 24–27.

* * * * *